(12) United States Patent
Desai et al.

(10) Patent No.: US 8,375,955 B2
(45) Date of Patent: Feb. 19, 2013

(54) SURGICAL PROCEDURE

(75) Inventors: Mihir M. Desai, Highland Heights, OH (US); Inderbir S. Gill, Beachwood, OH (US); Frank Bonadio, Bray (IE)

(73) Assignee: Atropos Limited, County Wicklow (IE)

( * ) Notice: Subject to any disclaimer, the term of this patent is extended or adjusted under 35 U.S.C. 154(b) by 180 days.

(21) Appl. No.: 12/700,859

(22) Filed: Feb. 5, 2010

(65) Prior Publication Data

US 2011/0011410 A1    Jan. 20, 2011

Related U.S. Application Data

(60) Provisional application No. 61/150,385, filed on Feb. 6, 2009.

(51) Int. Cl.
*A61B 19/00* (2006.01)

(52) U.S. Cl. ........................................ 128/898

(58) Field of Classification Search .............. 128/898; 600/204–209
See application file for complete search history.

(56) References Cited

U.S. PATENT DOCUMENTS

| | | | |
|---|---|---|---|
| 1,157,202 A | 10/1915 | McLeland |
| 1,598,284 A | 8/1926 | Kinney |
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |

(Continued)

FOREIGN PATENT DOCUMENTS

DE    37 39 532    12/1988
DE    37 37 121    5/1989

(Continued)

OTHER PUBLICATIONS

Kagaya, "Laparoscopic cholecystectomy via two ports, using the "Twin-Port" system", J. Hepatobiliary Pancreat Surg (2001) 8:76-80.

*Primary Examiner* — William H. Matthews
(74) *Attorney, Agent, or Firm* — Bookoff McAndrews, PLLC

(57) ABSTRACT

A surgical procedure is carried out on any suitable hollow organ, such as a gall bladder located beneath an abdominal wall. In a first step of the procedure the hollow organ is inflated by air or water through an inflation line so that the organ swells up. A scalpel is then used to create an incision in the abdominal wall. Sutures are then inserted through the opening and these are used to pull up the inflated organ to the opening. The inflated organ is now presented to the opening and a laparascopic procedure is carried out on the organ. A number of medical devices may be employed to perform the procedure for example a scalpel, an introducer device, an instrument access device, an insufflator, a camera device, and various surgical instruments.

19 Claims, 13 Drawing Sheets

U.S. PATENT DOCUMENTS

| | | |
|---|---|---|
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumuto et al. |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 4,998,930 A * | 3/1991 | Lundahl ........................ 606/15 |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Stouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroek |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,549,122 A * | 8/1996 | Detweilwer ................ 128/898 |
| 5,562,632 A | 10/1996 | Davila |

| Patent No. | Date | Name |
|---|---|---|
| 5,562,688 A | 10/1996 | Riza |
| 5,577,993 A | 11/1996 | Zhu et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroek |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,749,882 A | 5/1998 | Hart et al. |
| 5,755,660 A | 5/1998 | Tyagi |
| 5,769,783 A | 6/1998 | Fowler |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Watkins, III et al. |
| 5,832,925 A | 11/1998 | Rothrum |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Stouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,118,528 B1 | 10/2006 | Piskun |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049100 A1 | 3/2004 | Butler |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |

| | | | | | |
|---|---|---|---|---|---|
| 2004/0215063 A1 | 10/2004 | Bonadio et al. | GB | 1151993 | 5/1969 |
| 2004/0249248 A1 | 12/2004 | Bonadio et al. | GB | 1355611 | 6/1974 |
| 2005/0020884 A1 | 1/2005 | Heart et al. | GB | 1372491 | 10/1974 |
| 2005/0033246 A1 | 2/2005 | Ahlberg | GB | 1379772 | 1/1975 |
| 2005/0059865 A1 | 3/2005 | Kahle | GB | 1400808 | 7/1975 |
| 2005/0065543 A1 | 3/2005 | Kahle | GB | 1407023 | 9/1975 |
| 2005/0090713 A1 | 4/2005 | Gozales | GB | 1496696 | 12/1977 |
| 2005/0090716 A1 | 4/2005 | Bonadio et al. | GB | 2071502 | 9/1981 |
| 2005/0090717 A1 | 4/2005 | Bonadio et al. | GB | 2255019 | 10/1992 |
| 2005/0131349 A1 | 6/2005 | Albrecht | GB | 2275420 | 8/1994 |
| 2005/0148823 A1 | 7/2005 | Vaugh et al. | JP | 10-108868 | 4/1998 |
| 2005/0155611 A1 | 7/2005 | Vaugh et al. | JP | 11-290327 | 10/1999 |
| 2005/0159647 A1 | 7/2005 | Hart et al. | JP | 2001-61850 | 3/2001 |
| 2005/0192483 A1 | 9/2005 | Bonadio et al. | JP | 2002-28163 | 1/2002 |
| 2005/0192598 A1 | 9/2005 | Johnson | JP | 2004-195037 | 7/2004 |
| 2005/0197537 A1 | 9/2005 | Bonadio et al. | RU | 1342485 | 1/1997 |
| 2005/0203346 A1 | 9/2005 | Bonadio et al. | WO | WO 86/06272 | 11/1986 |
| 2005/0209510 A1 | 9/2005 | Bonadio et al. | WO | WO 92/11880 | 7/1992 |
| 2005/0240082 A1 | 10/2005 | Bonadio et al. | WO | WO 92/21292 | 12/1992 |
| 2005/0241647 A1 | 11/2005 | Nguyen | WO | WO 93/05740 | 4/1993 |
| 2005/0277946 A1 | 12/2005 | Greenhalgh | WO | WO 95/05207 | 2/1995 |
| 2005/0288558 A1 | 12/2005 | Ewers | WO | WO 95/07056 | 3/1995 |
| 2005/0288634 A1 | 12/2005 | O'Herron | WO | WO 95/22289 | 8/1995 |
| 2006/0020164 A1 | 1/2006 | Butler et al. | WO | WO 95/24864 | 9/1995 |
| 2006/0020241 A1 | 1/2006 | Piskun et al. | WO | WO 95/27445 | 10/1995 |
| 2006/0041270 A1 | 2/2006 | Lenker | WO | WO 95/27468 | 10/1995 |
| 2006/0047284 A1 | 3/2006 | Gresham | WO | WO 96/36283 | 11/1996 |
| 2006/0106402 A1 | 5/2006 | McLucas | WO | WO 97/32514 | 9/1997 |
| 2006/0149306 A1 | 7/2006 | Hart et al. | WO | WO 97/32515 | 9/1997 |
| 2006/0161050 A1 | 7/2006 | Butler et al. | WO | WO 98/35614 | 8/1998 |
| 2006/0247498 A1 | 11/2006 | Bonadio et al. | WO | WO 98/48724 | 11/1998 |
| 2006/0247499 A1 | 11/2006 | Butler et al. | WO | WO 99/03416 | 1/1999 |
| 2006/0247500 A1 | 11/2006 | Voegele et al. | WO | WO 99/25268 | 5/1999 |
| 2006/0264706 A1 | 11/2006 | Piskun | WO | WO 99/29250 | 6/1999 |
| 2007/0004968 A1 | 1/2007 | Bonadio et al. | WO | WO 00/32116 | 6/2000 |
| 2007/0049966 A1 | 3/2007 | Bonadio et al. | WO | WO 00/32117 | 6/2000 |
| 2007/0093695 A1 | 4/2007 | Bonadio et al. | WO | WO 00/32119 | 6/2000 |
| 2007/0118175 A1 | 5/2007 | Butler et al. | WO | WO 00/32120 | 6/2000 |
| 2007/0203398 A1 | 8/2007 | Bonadio et al. | WO | WO 00/35356 | 6/2000 |
| 2007/0255219 A1 | 11/2007 | Vaugh et al. | WO | WO 00/54675 | 9/2000 |
| 2008/0027476 A1 | 1/2008 | Piskun | WO | WO 00/54676 | 9/2000 |
| 2008/0097162 A1 | 4/2008 | Bonadio et al. | WO | WO 00/54677 | 9/2000 |
| 2008/0097163 A1 | 4/2008 | Butler et al. | WO | WO 01/08563 | 2/2001 |
| 2008/0200934 A1 * | 8/2008 | Fox ............................ 606/153 | WO | WO 01/08581 | 2/2001 |
| 2008/0255519 A1 | 10/2008 | Piskun et al. | WO | WO 01/26558 | 4/2001 |
| 2008/0281161 A1 | 11/2008 | Albrecht et al. | WO | WO 01/91652 | 12/2001 |
| 2008/0281162 A1 | 11/2008 | Albrecht et al. | WO | WO 02/17800 A2 | 3/2002 |
| 2009/0036745 A1 | 2/2009 | Bonadio et al. | WO | WO 02/34108 A2 | 5/2002 |
| 2009/0069837 A1 | 3/2009 | Bonadio et al. | WO | WO 03/026512 A1 | 4/2003 |
| 2009/0187079 A1 | 7/2009 | Albrecht et al. | WO | WO 03/034908 A3 | 5/2003 |
| | | | WO | WO 03/061480 A1 | 7/2003 |
| FOREIGN PATENT DOCUMENTS | | | WO | WO 03/103548 A1 | 12/2003 |
| DE | 296 00 939 | 6/1998 | WO | WO 2004/026153 | 4/2004 |
| EP | 0113520 | 7/1984 | WO | WO 2004/030547 A1 | 4/2004 |
| EP | 0142262 | 5/1985 | WO | WO 2005/009257 A2 | 2/2005 |
| EP | 0537768 | 4/1993 | WO | WO 2005/034766 A2 | 4/2005 |
| EP | 0950376 | 10/1999 | WO | WO 2006/040748 A1 | 4/2006 |
| EP | 1118657 | 7/2001 | | | |
| FR | 1456623 | 9/1966 | * cited by examiner | | |

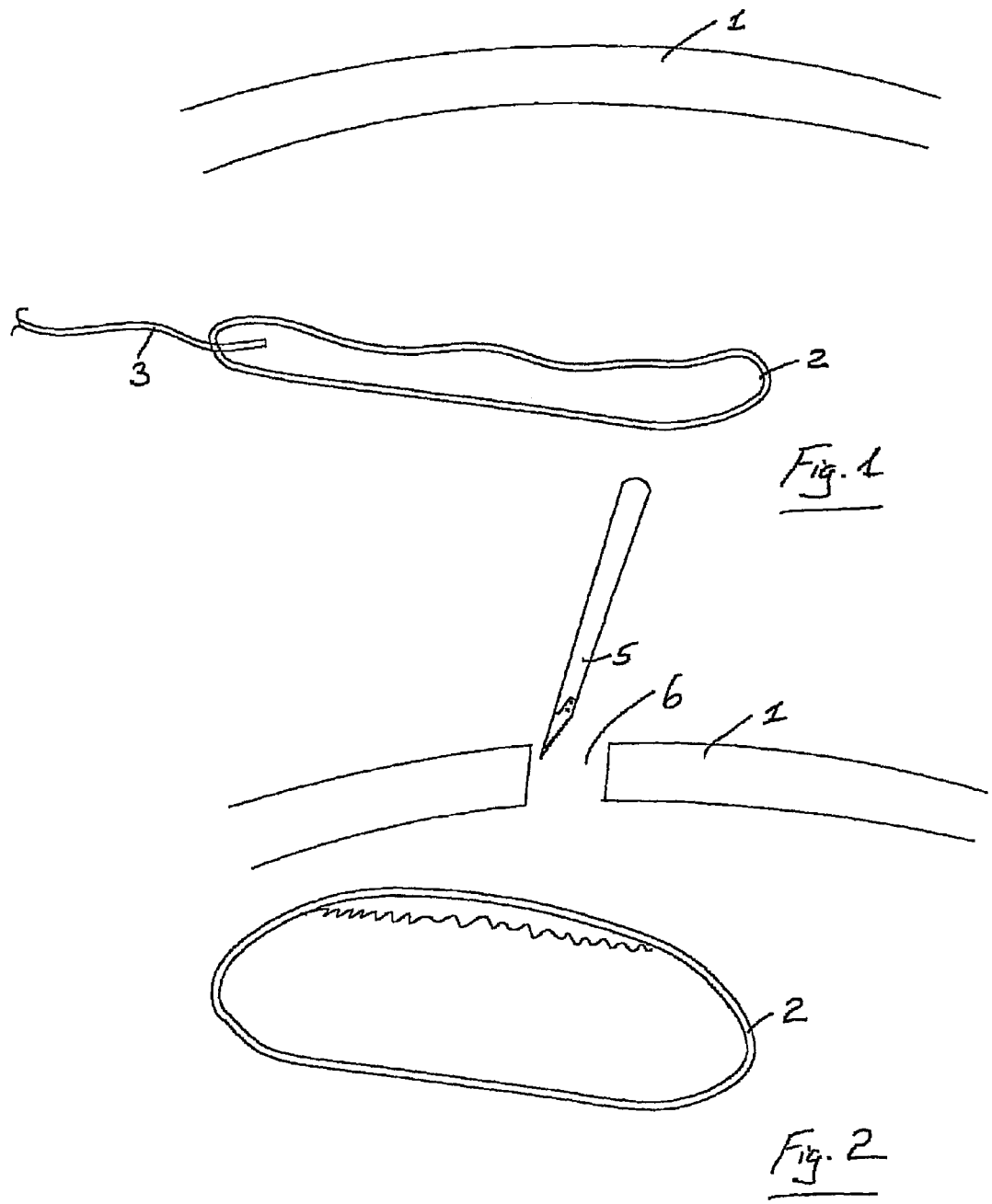

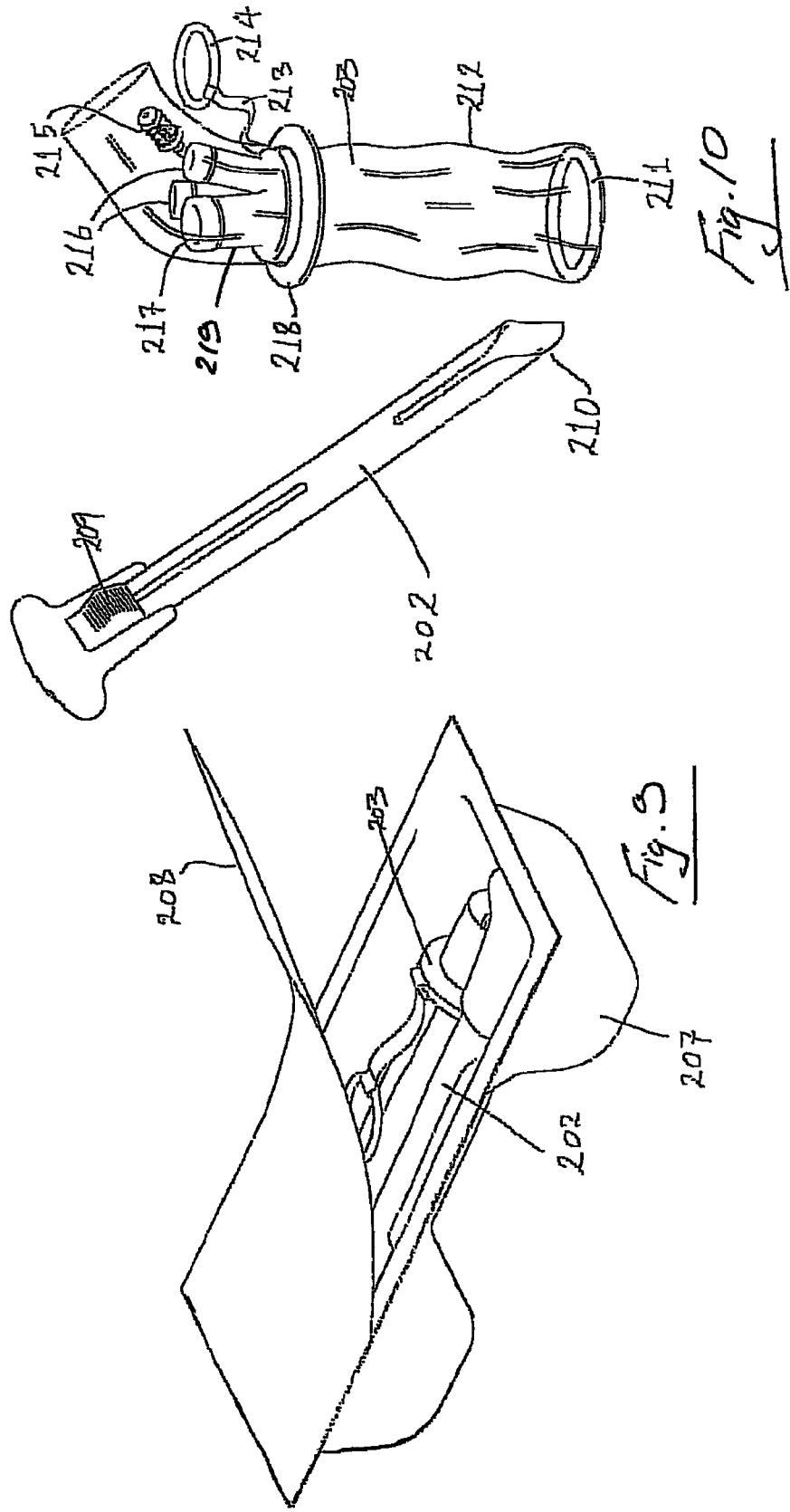

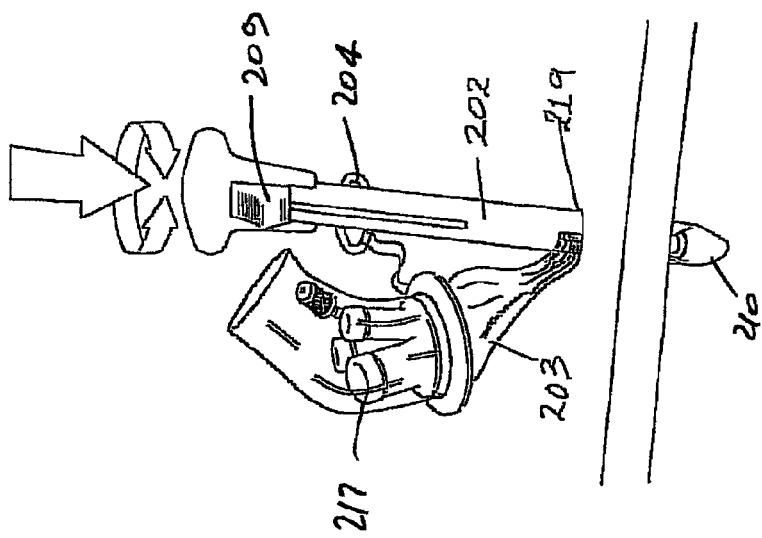
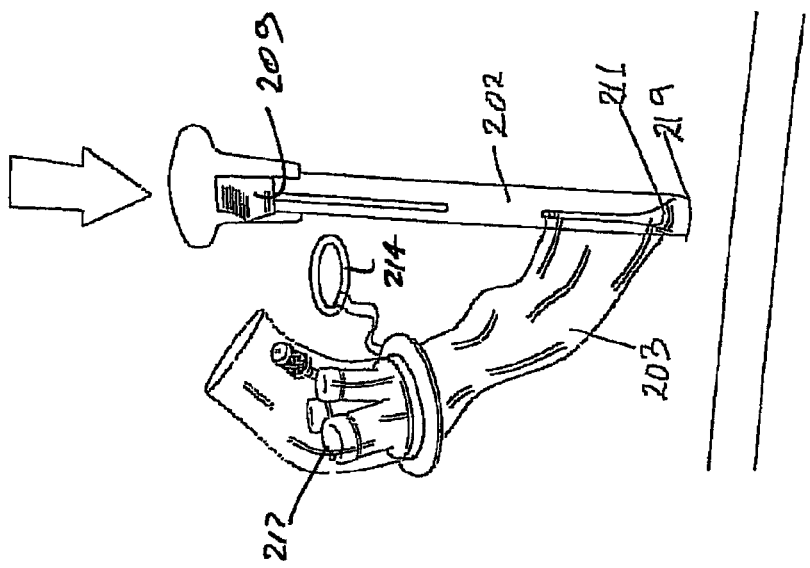

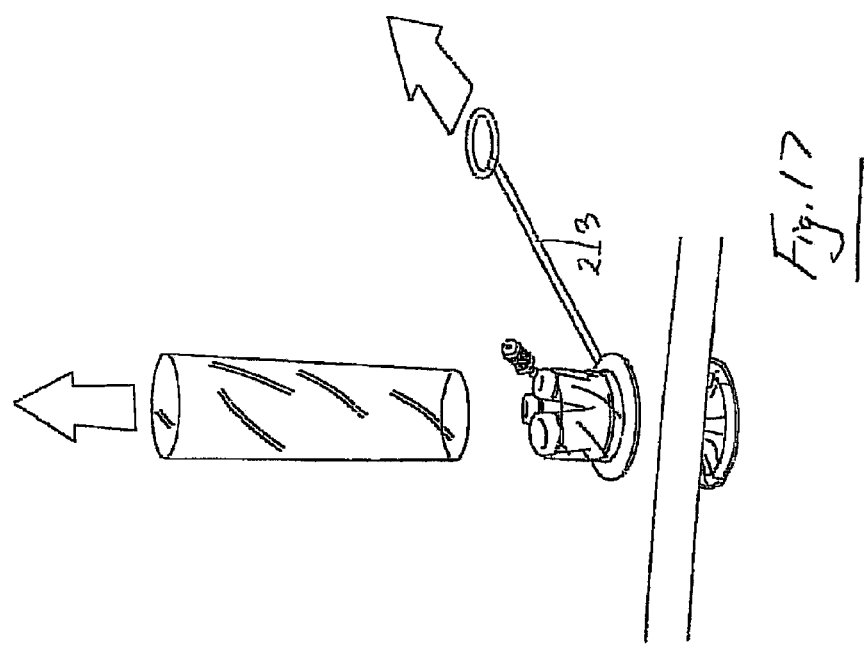
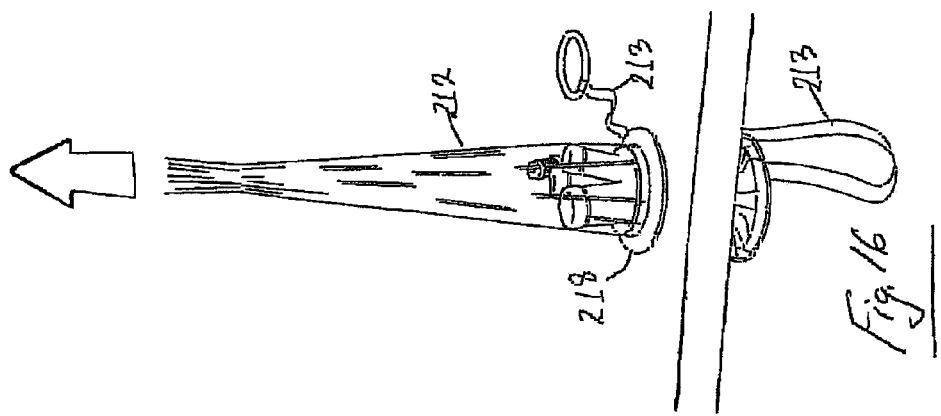

SURGICAL PROCEDURE

This application claims the benefit of U.S. Provisional Application No. 61/150,385 filed Feb. 6, 2009. The content of this provisional application is incorporated herein by reference.

INTRODUCTION

The invention relates to a method of performing a surgical procedure on a body organ such as the bladder, the uterus, the colon or the stomach.

To date surgical procedures on such organs involves major trauma to the patient with relatively long recovery times.

STATEMENTS OF INVENTION

According to the invention there is provided a method of carrying out a procedure in a hollow body organ comprising the step of:— inflating the hollow organ; and carrying out a procedure in the inflated hollow organ.

In one embodiment the hollow organ is inflated using a fluid such as air or water.

The hollow organ may be the bladder, the uterus, the stomach or the intestine.

In one embodiment the method comprises the step of making an incision to form a wound opening and presenting the inflated hollow organ to the wound opening.

In one case the method comprises the steps of engaging the inflated organ and pulling the inflated organ towards the wound opening. The inflated organ may be engaged by one or more sutures.

In one embodiment the method comprises the step of making an incision in the inflated organ to provide access to the interior of the organ.

The method may comprise:— providing an instrument access device comprising at least one instrument seal, a distal anchoring member, and a retractor member extending proximally from the distal anchoring member within the organ interior;

retracting laterally the sides of the opening in the organ using the retracting member; and inserting one or more surgical instruments through the instrument seal into the organ.

In one case the device is inserted at least partially through the wound opening using an introducer device. The method may comprise the step of inserting at least part of the access device into the introducer device.

In one case the method comprises the step of inserting the introducer device at least partially through the opening. The method may comprise the step of ejecting at least part of the instrument access device from the introducer device within the organ interior. The method may also comprise the step of removing the introducer device from the opening.

BRIEF DESCRIPTION OF THE DRAWINGS

The invention will be more clearly understood from the following description of some embodiments thereof, given by way of example only, with reference to the accompanying drawings, in which:—

FIGS. 1 to 8 are diagrams illustrating a method of performing a surgical procedure according to the invention;

FIG. 9 is an isometric view of a pack having an access device;

FIG. 10 is an isometric view of medical devices suitable for use in performing a surgical procedure according to the invention;

FIGS. 11 to 18 are isometric views illustrating insertion of an instrument access device into an opening.

DETAILED DESCRIPTION

Figure 3:
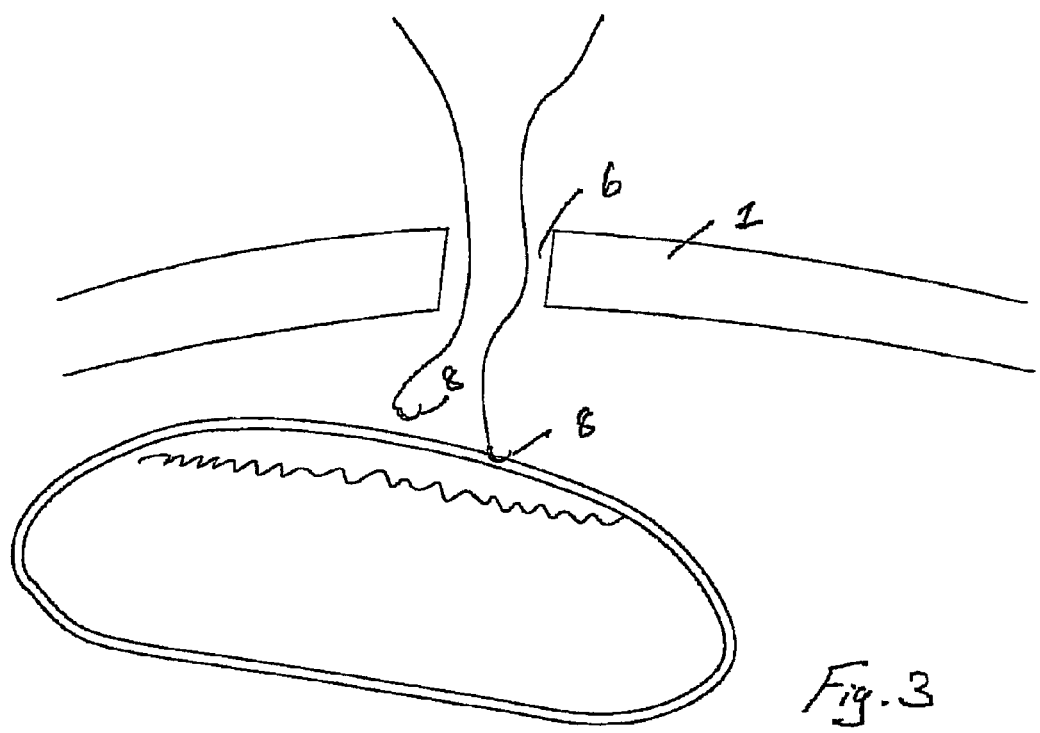

Referring to the drawings there is illustrated various steps in performing a surgical procedure according to the invention. The procedure can be carried out on any suitable hollow organ, such as a gall bladder located beneath an abdominal wall 1.

Figure 4:
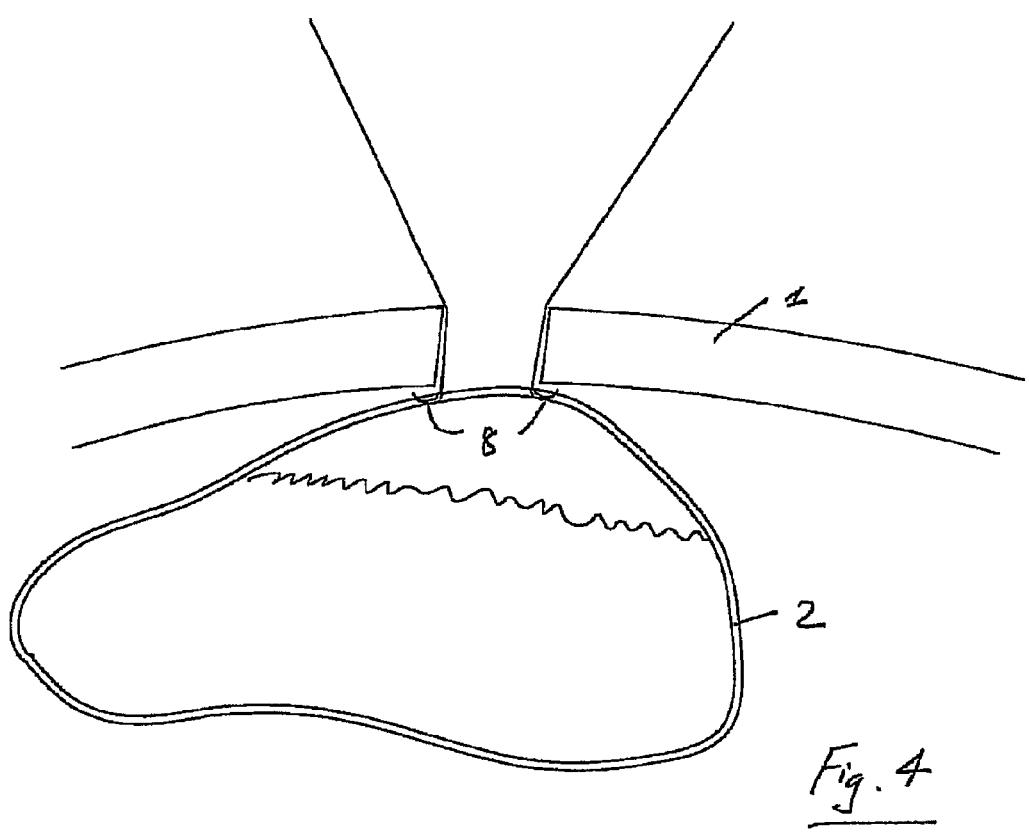
Figure 5:
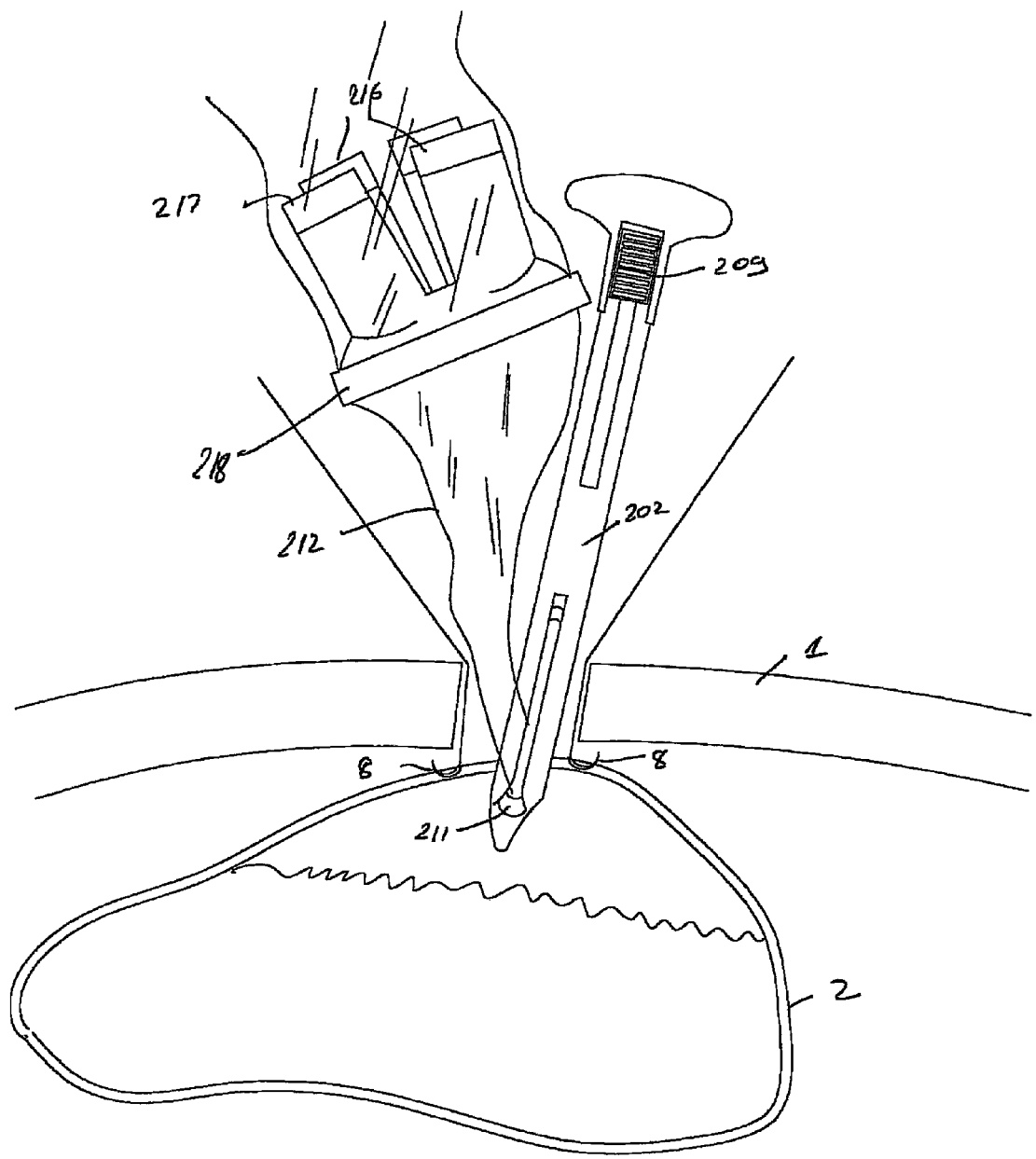
Figure 6:
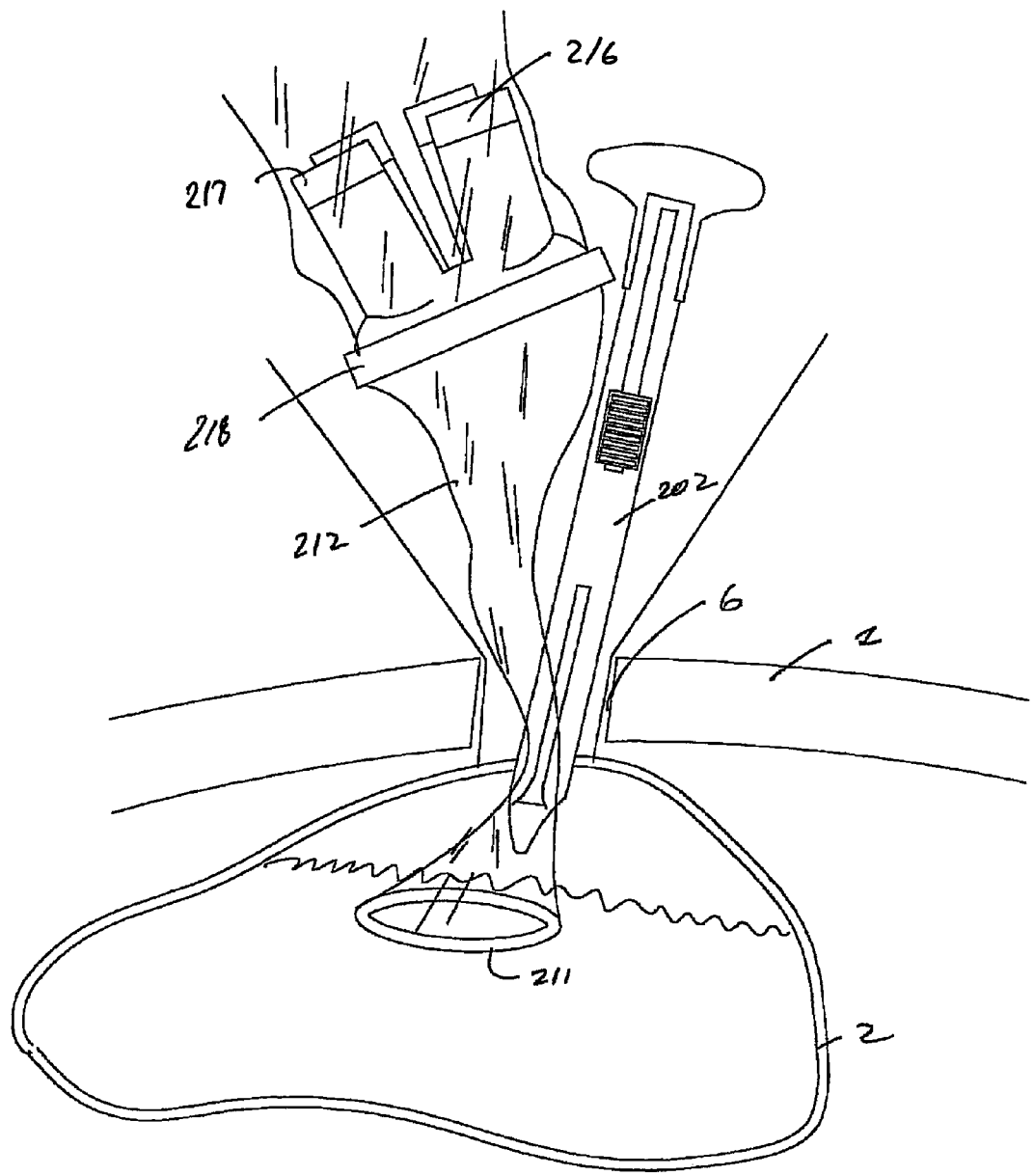
Figure 7:
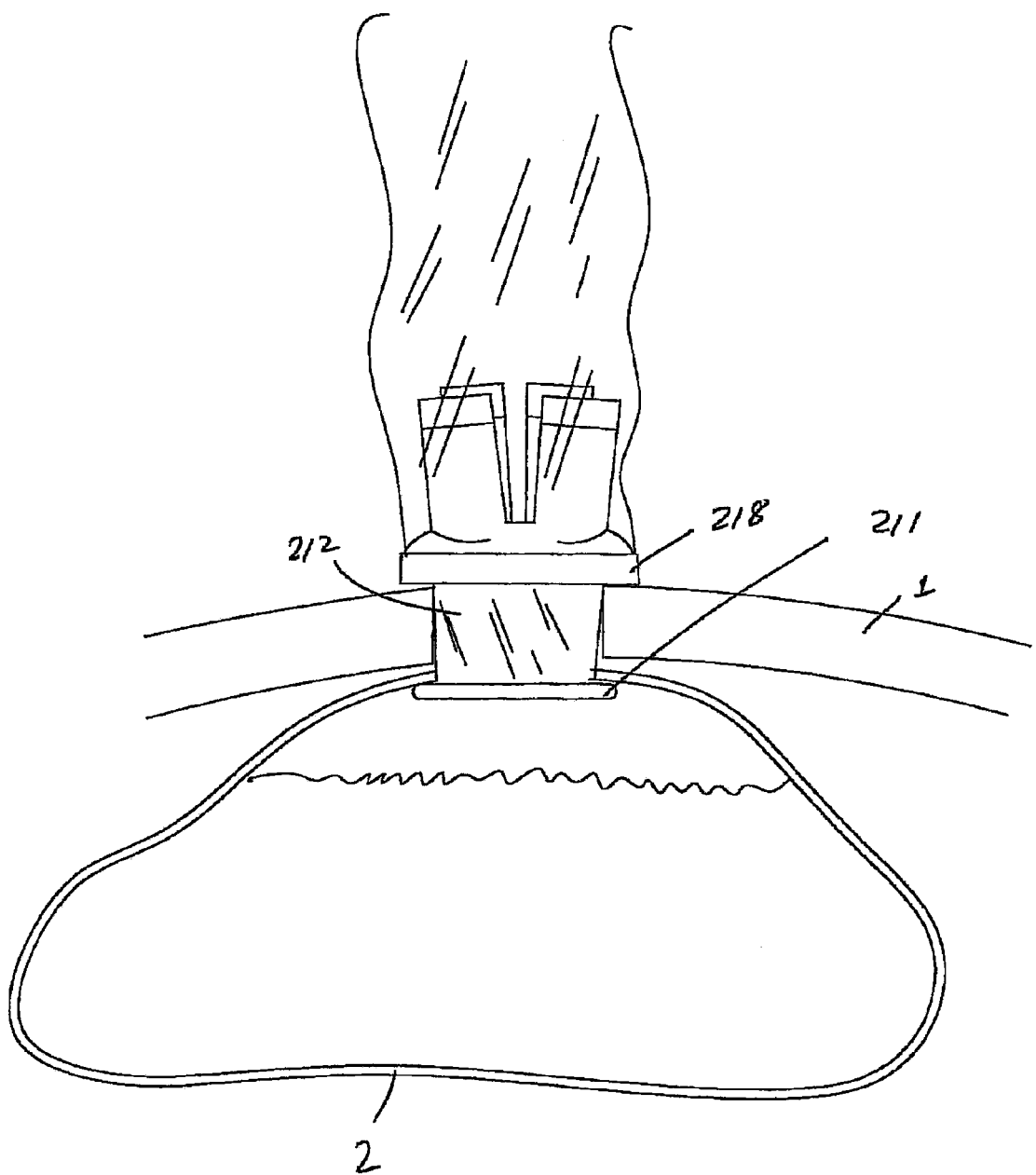
Figure 8:
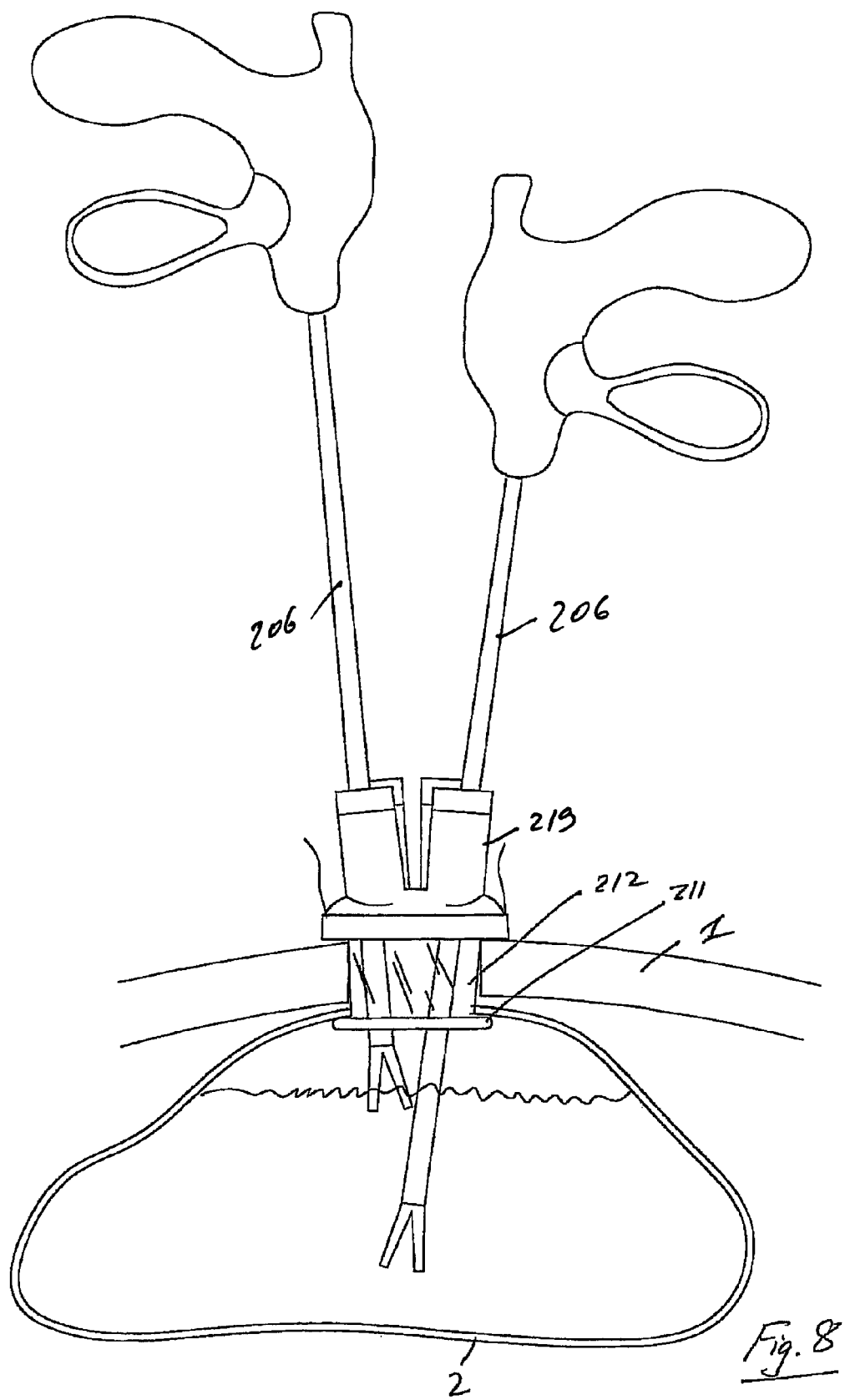

In a first step of the procedure the hollow organ 2 is inflated by air or water through an inflation line 3 so that the organ 2 swells up as illustrated in FIG. 2. A scalpel 5 is then used to create an incision 6 in the abdominal wall 1 [FIG. 2]. Sutures 8 are then inserted through the opening 6 [FIG. 3] and these are used to pull up the inflated organ 2 to the opening 6 [FIG. 4]. The inflated organ 2 is now presented to the opening 6 and a laparascopic procedure is carried out on the organ 2.

A number of medical devices may be employed to perform the procedure for example a scalpel 5, an introducer device 202, an instrument access device 203, an insufflator 204, a camera device 205, and various surgical instruments 206. For example medical devices described in US2009-0036745A may be employed. The entire contents of US2009-0036745A are incorporated herein by reference.

In use, the introducer device 202 and the instrument access device 203 are supplied in a pack 207. The pack 207 is opened (FIG. 9), and the introducer device 202 and the instrument access device 203 are removed from the pack 207 (FIG. 10).

FIG. 9 illustrates the peel off lid 208, the multiport access device 203, the injector introducer 202, and the plastic blister pack tray 207 which is a sterile pack. In FIG. 9 the user peels open the tray lid 208. FIG. 10 illustrates the injector introducer 202, the thumbswitch 209, the blunt dissecting tip 210, the distal ring 211, the sleeve 212, the removal ribbon 213, the removal ring 214, the insufflation line 215, the 5 mm ports 216, the 12 mm port 217, and the outer proximal ring 218. In FIG. 10 the user removes the introducer 202, and the multiport access device 203.

Figure 11:
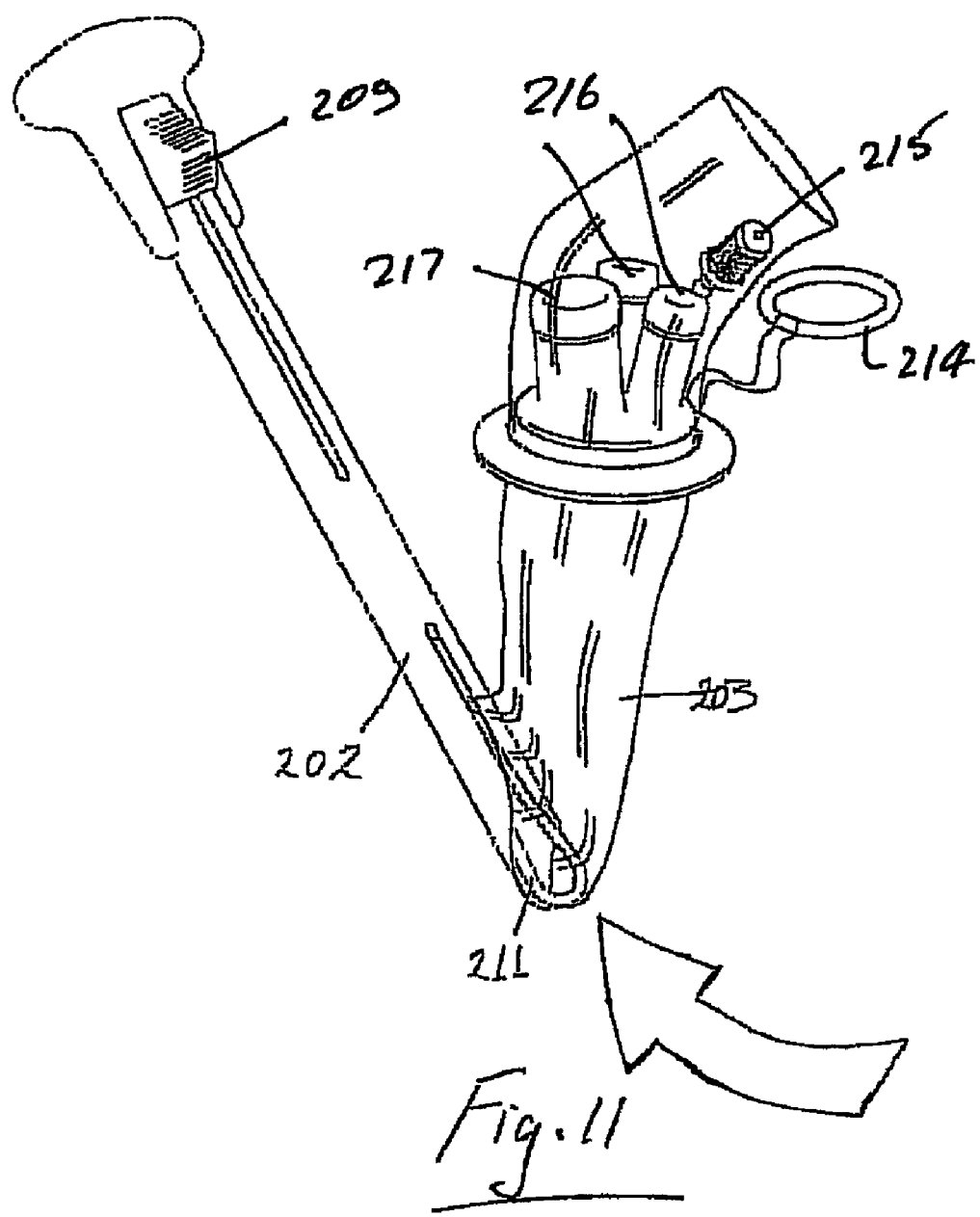

The distal ring 211 of the instrument access device 203 is inserted into the introducer device 202 (FIG. 11). A scalpel may be used to create an opening in the hollow inflated organ 2.

In FIG. 11 the user inserts the distal ring 211 into the end of the injector introducer 202.

The introducer device 202 is inserted through the opening in the organ 2 until the distal ring 211 of the instrument access device 203 is within the interior (FIGS. 12 and 13).

In FIG. 12 the tip of the injector introducer 202 is placed in the incision in the organ. Downward pressure and axial rotation of the injector introducer 202 cause the blunt dissecting tip 210 to burrow through into the organ (FIG. 13).

Figure 15:
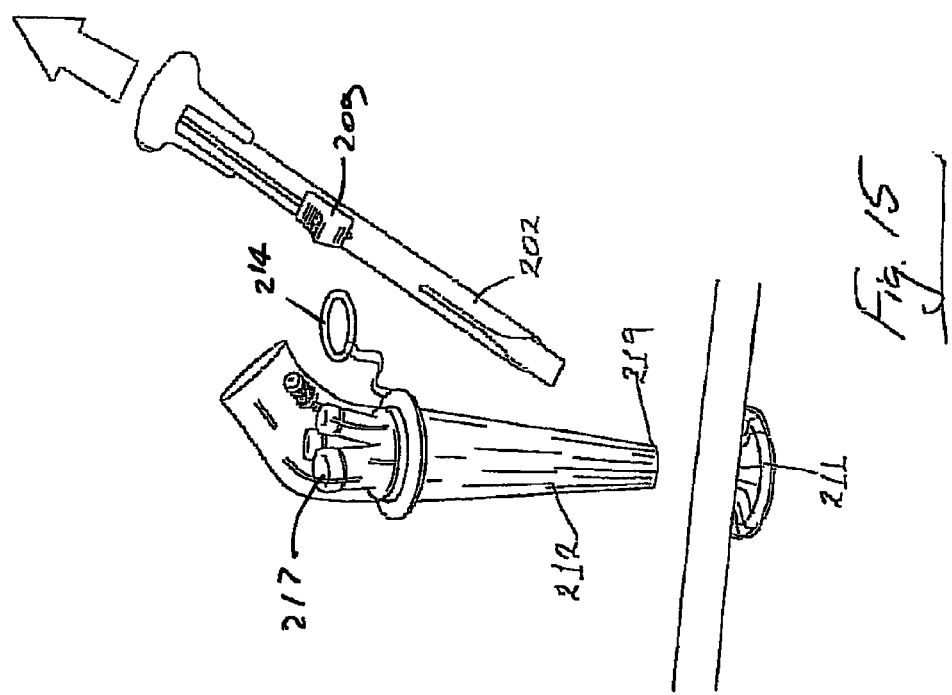

The thumbswitch 209 of the introducer device 202 is depressed to eject the distal ring 211 of the instrument access device 203 into the organ interior (FIG. 14), and the introducer device 202 is removed from the organ opening 219 (FIG. 15).

Figure 14:
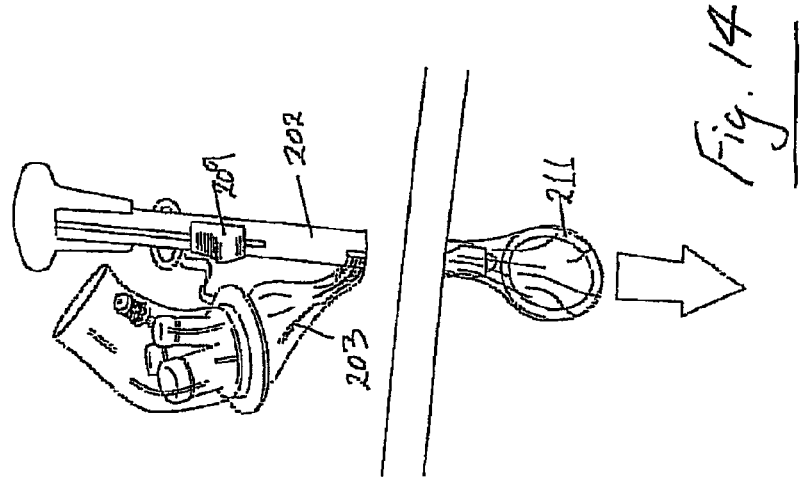

In FIG. 14 the thumbswitch 209 is pressed downwards to eject the distal ring 211. In FIG. 15 the injector introducer 202 is removed from the incision 219 leaving the distal ring 211 in the inflated organ 2. The sleeve 212 is pulled upwards to engage the distal ring 211 with the underside of the organ wall.

The sleeve 212 of the instrument access device 203 is pulled proximally and the outer proximal ring 218 is pushed distally to retract laterally the sides of the organ opening 219 (FIG. 16). The excess sleeve material is cut-away, and the removal ribbon 213 is pulled proximally to remove any excess ribbon from the organ interior (FIG. 17).

In FIG. 16, the user keeps upward tension on the sleeve 212, and the outer proximal ring 218 is pushed down until sufficient retraction is achieved. In FIG. 17 the removal ribbon 213 is gently pulled to remove slackness from inside the organ. The excess sleeve 212 is cut and removed.

Figure 19:
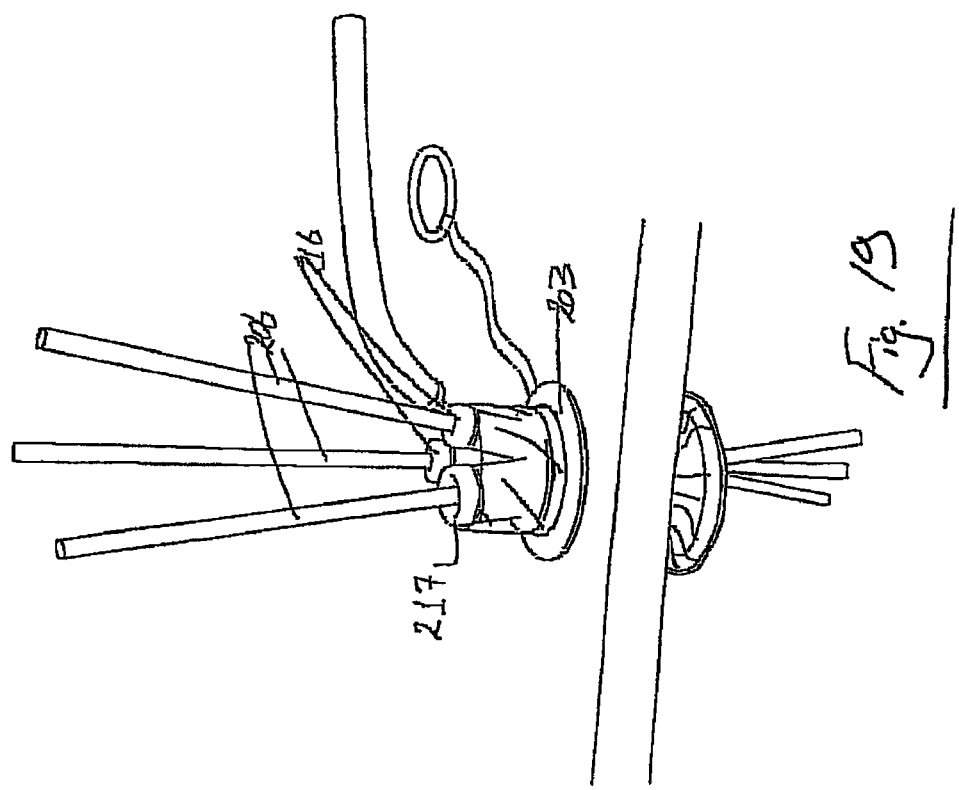
FIGS. 19 and 20 are isometric views illustrating performing a surgical procedure using surgical instruments inserted through the instrument access device of FIGS. 11 to 18.

An insufflator 204 may be connected to the insufflation line 215 to further insufflate the organ (FIG. 18), and one or more instruments 206 may be inserted through the ports 216, 217 (FIG. 19).

Figure 18:
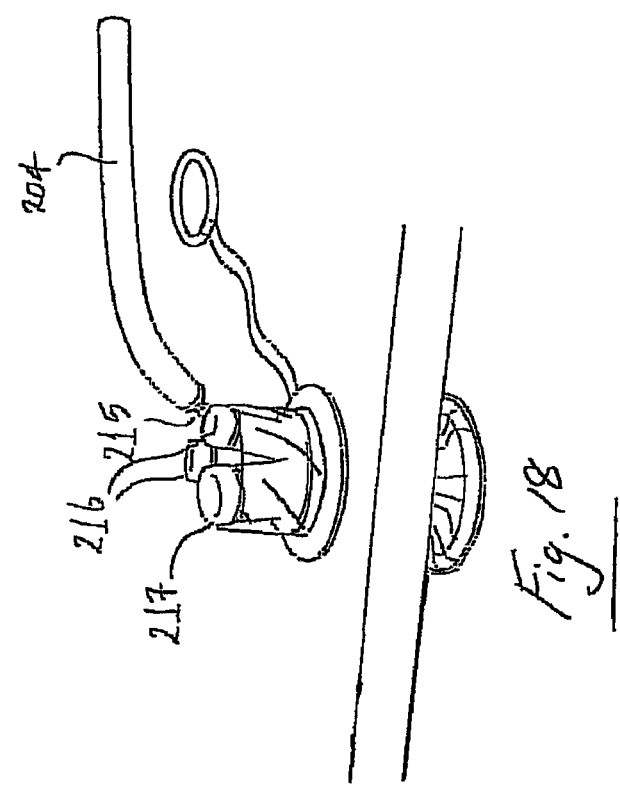

FIG. 18 illustrates the insufflation supply 204, the insufflation line 215, the gel ports 216, 217. In FIG. 18 the insufflation line 215 is attached to the insufflation supply 204. In FIG. 19 up to three instruments 206 may be used simultaneously through the multiport device 203. Each leg 216, 217 have an individual valve on top. The legs 216, 217 are rubbery and so can accommodate the instruments 206 moving off axis. Moving one instrument 206 does not cause leaks in either of the other two instruments 206.

Figure 20:
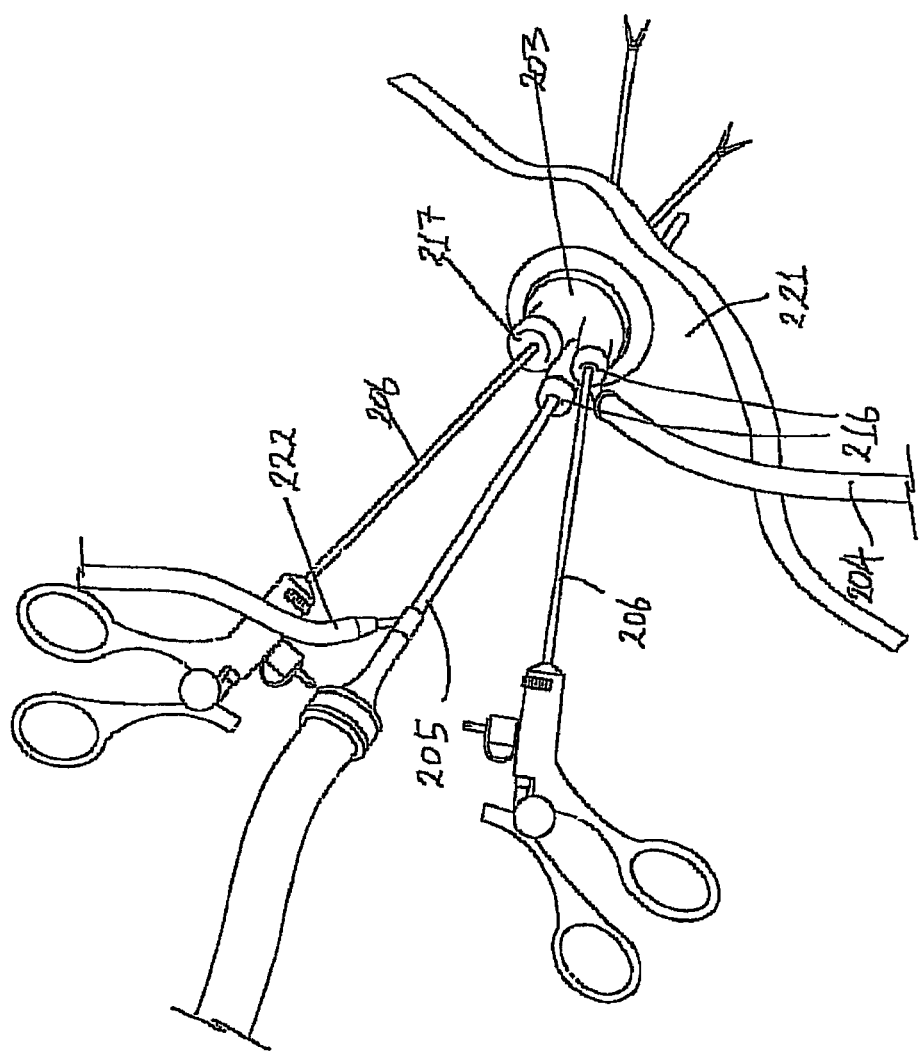

Instruments 206 may be inserted through the ports 216, 217 of the instrument access device 203 to access the organ interior, and/or the camera 205 may be inserted through one of the ports 216, 217 to access the organ interior (FIG. 20). In this case the camera 205 has a light source 222 inclined at an angle to the longitudinal axis of the camera 205, and the instruments 206 are straight.

In FIG. 20 there are two 5 mm ports 216 and one 12 mm port 217. FIG. 38 illustrates the 5 mm camera 205, the 5 mm instruments 206, the insufflation supply 204, the organ wall 221, and the 12 mm port 217.

The device comprises a distal anchoring ring 211, a retractor member 212, a proximal ring assembly 218, a connector sleeve, and instrument seals 216, 217. One such retractor is described in our US 2005-0090717 A, the entire contents of which are incorporated herein by reference.

The distal anchoring ring 211 is located within a wound interior, in use. In this case the distal, anchoring ring 211 is provided in the form of an O-ring.

The proximal ring assembly 218 is located externally of a wound opening, in use. The proximal ring assembly 218 may comprise an inner ring part and an outer ring part. In one case the inner ring part is provided in the form of an O-ring.

The retractor member 212 may be employed to retract laterally the sides of a wound opening. The retractor member 212 may extend between the distal anchoring ring 211 and the proximal ring assembly 218 in two layers. A first end of the retractor member is fixed to the inner ring part. The retractor member 212 extends distally from the inner ring part to the distal anchoring ring 211, is looped around the distal anchoring ring 211, extends proximally from the distal anchoring ring 211 to the proximal ring assembly, and extends proximally between the inner ring part and the outer ring part. The retractor member 212 is slidably movable relative to the distal anchoring ring 211, and a second end of the retractor member is slidably movable between the inner ring part and the outer ring part. In this case the retractor member is provided in the form of a sleeve.

In one case a retractor comprises a distal anchoring ring in the form of an O-ring 211. A retractor member comprises a sleeve 212 which in this case extends in two layers between the distal anchoring ring 211 and a proximal ring assembly 218.

The device comprises instrument seals 216, 217. Connector sleeves 219 extend from the seals 216, 217 to the proximal assembly.

Each instrument seal 216, 217 may be employed to effect a seal around a separate instrument extended through the device. Each instrument seal 216, 217 is formed separately from the other instrument seals, and is spaced apart from the other instrument seals. A first instrument seal may have a diameter equal to the diameter of a second instrument seal. The third instrument seal may have a larger diameter than the second instrument seal.

Each connector sleeve 219 connects the proximal ring assembly to one of the instrument seals 216, 217. Each connector sleeve 219 is inclined relative to the proximal ring assembly.

Each instrument seal 216, 217 comprises a sealing part which may be of a gelatinous elastomeric material, and a mounting part of a rigid material. The sealing part effects a seal around an instrument extended through the device. The mounting part facilitates releasable mounting of the instrument seal 216, 217 to the connector sleeve 219 in a gas-tight manner. The mounting part may comprise an outwardly protruding barb for an interference fit between the mounting part and the connector sleeve. The sealing part may be overmoulded over part of the mounting part to connect the sealing part to the mounting part.

The device comprises a connector base to releasably mount the connector sleeves 219 to the proximal assembly in a gas-tight manner. The base may comprise outwardly protruding ridges for an interference fit between the base and the inner ring part. A rigid reinforcement ring may be embedded within the base to reinforce the base.

The invention facilitates extraction of organs or parts thereof without contamination of the body wall.

Various features of the invention are described and illustrated. It will be appreciated that at least some of the features described in relation to one embodiment may be used not only in the embodiment specifically described but also in other appropriate embodiments.

The invention is not limited to the embodiments hereinbefore described, with reference to the accompanying drawings, which may be varied in construction and detail.

The invention claimed is:

1. A method of carrying out a procedure in a hollow body organ comprising the step of:
    inflating the hollow organ;
    carrying out a procedure in the inflated hollow organ;
    providing an instrument access device comprising
        at least one instrument seal,
        a distal anchoring member, and
        a retractor member extending proximally from the distal anchoring member within the organ interior;
    retracting laterally sides of an opening in the organ using the retracting member; and
    inserting one or more surgical instruments through the instrument seal into the organ.

2. A method as claimed in claim 1 wherein the hollow organ is inflated using a fluid.

3. A method as claimed in claim 2 wherein the hollow organ is inflated using air or water.

4. A method as claimed in claim 1 wherein the hollow organ is selected from the bladder, the uterus, the stomach and the colon.

5. A method as claimed in claim 1. further comprising making an incision to form a wound opening and providing access to the inflated hollow organ through the wound opening.

6. A method as claimed in claim 5, further comprising engaging the inflated organ and pulling the inflated organ towards the wound opening.

7. A method as claimed in claim 6 wherein the inflated organ is engaged by one or more sutures.

8. A method as claimed in claim 1, further comprising making an incision in the inflated organ to provide access to the interior of the organ.

9. A method as claimed in claim 1, wherein the device is inserted at least partially through the wound opening using an introducer device.

10. A method as claimed in claim 9, further comprising inserting at least part of the instrument access device into the introducer device.

11. A method as claimed in claim 9, further comprising inserting the introducer device at least partially through the opening.

12. A method as claimed in claim 11, further comprising ejecting at least part of the instrument access device from the introducer device within the organ interior.

13. A method as claimed in claim 11, further comprising removing the introducer device from the opening.

14. A method of carrying out a procedure in a hollow body organ, comprising:
  carrying out a procedure in the hollow organ inflated by inflation material;
  providing an instrument access device comprising
    at least one instrument seal,
    a distal anchoring member, and
    a retractor member extending proximally from the distal anchoring member within the organ interior;
  inserting the instrument access device at least partially through a wound opening;
  retracting laterally sides of an opening in the organ using the retracting member; and
  inserting one or more surgical instruments through the instrument seal into the organ.

15. A method of carrying out a procedure in a hollow body organ, comprising:
  supplying inflation material to the hollow organ;
  making an incision in the inflated organ to provide access to the interior of the organ;
  providing an instrument access device comprising
    at least one instrument seal,
    a distal anchoring member and
    a retractor member extending proximally from the distal anchoring member within the organ interior;
  retracting laterally sides of an opening in the organ using the retracting member; and
  inserting one or more surgical instruments through the instrument seal into the organ.

16. A method as claimed in claim 14, wherein the hollow organ is chosen from the bladder, uterus, stomach and colon.

17. A method as claimed in claim 15, wherein the hollow organ is selected from bladder, uterus, stomach and colon.

18. A method as claimed in claim 15, further comprising supplying the inflation material through an inflation line to the hollow organ.

19. A method as claimed in claim 15, further comprising inserting the instrument access device at least partially through the wound opening using an introducer device.

\* \* \* \* \*